United States Patent
Schubart et al.

(10) Patent No.: US 10,368,737 B2
(45) Date of Patent: Aug. 6, 2019

(54) METHOD FOR DETERMINING VISUAL ACUITY

(71) Applicant: Rodenstock GmbH, Munich (DE)

(72) Inventors: Johannes Schubart, Diesenhofen (DE); Peter Seitz, Munich (DE); Killian Perani, Munich (DE)

(73) Assignee: Rodenstock GmbH, Munich (DE)

( * ) Notice: Subject to any disclaimer, the term of this patent is extended or adjusted under 35 U.S.C. 154(b) by 125 days.

(21) Appl. No.: 15/322,061

(22) PCT Filed: May 7, 2015

(86) PCT No.: PCT/EP2015/000935
§ 371 (c)(1),
(2) Date: Dec. 23, 2016

(87) PCT Pub. No.: WO2015/197149
PCT Pub. Date: Dec. 30, 2015

(65) Prior Publication Data
US 2017/0135571 A1    May 18, 2017

(30) Foreign Application Priority Data
Jun. 25, 2014 (DE) ........................ 10 2014 009 459

(51) Int. Cl.
*A61B 3/02* (2006.01)
*A61B 3/032* (2006.01)
(Continued)

(52) U.S. Cl.
CPC ............ *A61B 3/032* (2013.01); *A61B 3/0025* (2013.01); *A61B 3/0041* (2013.01); *A61B 3/028* (2013.01); *A61B 3/036* (2013.01)

(58) Field of Classification Search
CPC ....... A61B 3/0025; A61B 3/028; A61B 3/032; A61B 3/0041; A61B 3/036
(Continued)

(56) References Cited

U.S. PATENT DOCUMENTS 6,238,049 B1    5/2001  Griffin et al.
2003/0218721 A1  11/2003 Stern et al.
(Continued)

FOREIGN PATENT DOCUMENTS

EP    2561799         2/2013
JP    2003-088501 A   3/2003
(Continued)

OTHER PUBLICATIONS

European Patent Office, International Search Report issued for PCT/EP2015/000935 dated Jul. 28, 2015, 4 pgs. (German language only).
(Continued)

*Primary Examiner* — Hung X Dang
(74) *Attorney, Agent, or Firm* — Schiff Hardin LLP

(57) ABSTRACT

In a method for providing optotypes for determining distance visual acuity, a test subject position is provided for a test subject and a display surface at a display position. An individual test distance between the test subject position and the display position is, for example, detected automatically. An individual target variable is determined for optotypes which are matched to the detected individual test distance according to a predetermined role. Digital optotype image data are provided which contain optotypes scaled to the individual target variable. The digital optotype image data are displayed on the display surface.

16 Claims, 1 Drawing Sheet

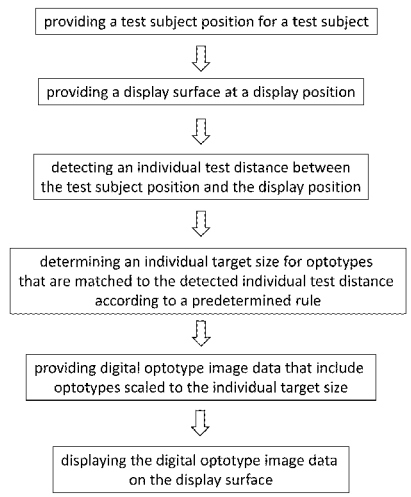

(51) Int. Cl.
 *A61B 3/028* (2006.01)
 *A61B 3/036* (2006.01)
 *A61B 3/00* (2006.01)

(58) Field of Classification Search
 USPC .................. 351/237, 238, 239, 240, 246
 See application file for complete search history.

(56) References Cited

U.S. PATENT DOCUMENTS

| | | |
|---|---|---|
| 2008/0259278 A1 | 10/2008 | Nozawa et al. |
| 2012/0212706 A1 | 8/2012 | Chou et al. |
| 2013/0128229 A1 | 5/2013 | Huang |
| 2013/0301007 A1* | 11/2013 | Wolffsohn ............. A61B 3/032 |
| | | 351/239 |

FOREIGN PATENT DOCUMENTS

| | | |
|---|---|---|
| JP | 2009-178500 A | 8/2009 |
| JP | 2011-224198 A | 11/2011 |
| JP | 2012-525948 A | 10/2012 |
| WO | WO 2008/064379 | 6/2008 |

OTHER PUBLICATIONS

Office Action dated Dec. 7, 2018 for Japanese Patent Application No. 2016-575043 (with English translation).

\* cited by examiner providing a test subject position for a test subject

providing a display surface at a display position

detecting an individual test distance between the test subject position and the display position

determining an individual target size for optotypes that are matched to the detected individual test distance according to a predetermined rule

providing digital optotype image data that include optotypes scaled to the individual target size

displaying the digital optotype image data on the display surface

METHOD FOR DETERMINING VISUAL ACUITY

The invention concerns a method for providing optotypes; a method for determining optical correction values of a test subject; a computer program product; and a mobile computer.

Refraction is used to determine correction values of an ametropic test subject. Optotypes in various shapes are thereby shown to the test subject. These thereby serve to determine the visual acuity and the contrast capability of the test subject. Moreover, the accommodation equilibrium, the color vision or the binocular status may be checked by means of additional vision tests.

To conduct these tests, either classical test panels are used that must be set up at a predetermined distance from the test subject, or expensive refraction units are used that present the vision tests via projectors that are to be manually calibrated. The devices are thereby permanently installed. In particular given vision tests for distance (thus for vision tests as of a testing distance of at least one meter, in particular of at least four meters) or in vision tests with a shortened testing distance (for examine given house calls or at events), can be [sic] realized only with great effort, or by taking along multiple test panels. Some vision tests (for example a red-green test) are no longer available as test panels. Other vision tests (for example what are known as the Vistech panels and the Pelli Robson charts) are no longer produced as test panels and therefore can only be obtained with great difficulty, are available only as remainder stock, or are no longer available at all.

The process of subjective refraction has been thoroughly discussed many times in the technical literature. There are also manuals and publications regarding the utilization of test panels and refraction units. In refraction, a differentiation is made between determination of visual acuity close up (at a distance of approximately 25 cm to approximately 60 cm) and determination of visual acuity for distance (which is normally conducted at a distance of at least four meters). If a patient or customer has severe ametropia or special requirements, a vision test may also be conducted at reduced distances.

Permanently installed refraction units have a large space requirement, high procurement costs from 10000 to 20000 EUR, and may only be transported and used in a mobile manner with very large effort.

Although test panels are more manageable than refraction units, test panels are not available for all vision tests. An additional disadvantage of test panels is their limited durability and appearance of wear given transport.

Both previously known methods for conducting a vision test have the disadvantage that they must be manually calibrated for a predetermined test distance or are specifically produced for this. If this test distance is changed, or if this test distance can no longer be maintained, the tester must convert the obtained results in the reading of the optotypes in order to obtain corresponding specifications for the visual acuity etc. which then apply to the vision test with modified test distance.

The invention is based on the object of enabling a simplified determination of distance visual acuity. The invention is in particular based on the object of enabling a determination of distance visual acuity for a variable test distance and/or for mobile use.

This object is achieved via the subject matters of the independent Claims. Preferred embodiments are the subject matters of the dependent Claims.

One aspect pertains to a method for providing optotypes for a determination of distance visual acuity, with the steps:
provide a test subject position for a test subject,
provide a display surface at a display position,
detect an individual test distance between the test subject position and the display position,
determine an individual target size for optotypes which are matched to the detected individual test distance according to a predetermined rule,
provide digital optotype image data that include optotypes scaled to the individual target size, and
display the digital optotype image data on the display surface.

FIG. 1 is an example method for providing and displaying optotype image data, in accordance with an embodiment of the disclosure.

Via the method, as depicted in FIG. 1, for example, what are known as optotypes are provided whose size is matched to the individual test distance. The individual test distance is thereby dynamic and/or variable.

To provide the test subject position, a test position is established at which a test subject should stay during implementation of a determination of visual acuity as a vision test. For example, a seat may be provided for this on which the test subject may situation while the planned vision test is being conducted. The test subject position may also be provided to determine another location for the test subject, for example by marking a standing space or the selection of a reclining space (for bedridden test subjects, for example). The provision of the test subject position thus corresponds to the determination of a stay location at which the test subject may stay while the planned vision test is being conducted. Vision tests are regularly conducted with the aid of refraction spectacles that the test subject wears during the vision test. With refraction spectacles, different test lenses may be placed in front of them until the ametropia correction that is subjectively perceived to be best for the test subject has been found. This is hereby called the subjective refraction.

The test subject position may be more precisely defined as a position of the refraction spectacles while conducting the test, thus on the nose of the test subject. Alternatively, the test subject position may also be defined as an eye position of the test subject during the test.

A display surface on which digital image data may be directly displayed—for example a monitor, a screen, a projection screen, a television screen, a display of a mobile computing device etc.—is preferably selected as a display surface.

By establishing the test subject position and the display position, the individual test distance that corresponds to the distance of the test subject position from the display position is established and defined. The individual test distance may be detected automatically, for example.

The individual target size for optotypes which are located at a distance from the test subject that corresponds to the individual test distance is determined depending on the detected individual test distance. The target size of the optotypes that is to be determined may include an area, a height, a width and/or a diameter of the optotypes. Since a plurality of optotypes that may have different sizes are normally used to conduct a vision test, different individual target sizes may also be determined in this step. For example, for each optotype a specific individual target size of the optotype that is associated with said optotype may thereby be determined. Alternatively or additionally, only a scaling factor may also be established as a target size for digital images, for example of digital images of test panels that are prepared in advance, which test panels have optotypes and are designed and provided to conduct a vision test. For example, these digital images of optotypes may include optotypes at a size that are designed for a predetermined test distance. The scaling factor for these digital images of test panels that are prepared in advance may, for example, be specified in percent in order to scale the associated image data in percentiles, and thus to either enlarge or reduce depending on the detected individual test distance.

For example, a predetermined angle at which the optotypes should appear to the test subject at the individual test distance may serve as a predetermined rule. The dependency of such a target size on the test distance is provided in the European standard EN ISO 8596:2009 and in the German standard DIN 58220-5, for example. In particular, a standardized target size may thus in particular serve as a predetermined rule, for example the target size for Landolt rings that is standardized according to the enumerated standards. In the standards, the angle of appearance of the Landolt rings represents a predetermined rule from which the size of the Landolt rings may be calculated for the detected individual test distance as an individual target size of the optotypes.

After determining the target size, digital optotype image data are prepared that include optotypes scaled to the individual target size. The digital optotype image data are designed and provided to be displayed on the display surface. If the digital optotype image data are displayed on the display surface, the optotypes are displayed at the individual target size associated with them. Considered from the test subject position, the displayed optotypes thus have precisely that target size that they should have according to the predetermined rule (for example a standard) that is used. A vision test—in particular a determination of distance visual acuity—may therefore be conducted using the displayed optotypes. The method may be implemented without cumbersome refraction units and without classical, pre-printed test panels. The optotypes may be matched to a dynamically variable, individual test distance as a test spacing, in particular with the aid of a computer or computer-like device.

According to one embodiment, the determination of the individual target size for optotypes, the provision of the digital optotype image data and the display of the digital optotype image data are implemented automatically by means of a mobile computer. A laptop, a notebook, a tablet computer, a smartphone or a similar electronic device, having a microprocessor on which runs an operating system that can execute the programs, may thereby be used as a mobile computer. For example, after automatic detection of the individual test distance, the mobile computer may calculate the individual target size depending on the individual test distance and prepare the digital optotype image data. The generated digital optotype image data may either be displayed on the display of the computer or be provided to a data output of the computer, in particular to a wireless output.

The mobile computer thus includes all or nearly all essential device articles that [sic] to conduct the determination of distance visual acuity. Carrying along test panels or a refraction unit is therefore superfluous. The implementation of the method is thereby simplified and/or made possible for the first time in house calls and at public events, for example.

Alternatively, a stationary computer such as a desktop PC or tower PC (which, however, is more complicated to transport) may also be used.

According to one embodiment, an individual test dot pitch in digital image data is determined at the display surface. The digital optotype image data are scaled to the target size under consideration of the individual test dot pitch. To determine the individual test dot pitch, a test image that includes at least two prominent test dots that are simple to identify may be displayed on the display surface. Via the determination of the individual test dot pitch, it may be established what spacing two points in the digital image (thus the digital image data) actually have from one another on the display surface. For example, the test dot pitch may be specified in a length unit, such as in centimeters. Knowledge of the individual test dot pitch on the display surface enables a conversion of pixel pitches in digital image data into the actual real pitch length of the corresponding image points that are displayed on the display surface. The individual test dot pitch serves for calibration of the size of the optotypes that should be displayed on the display surface.

In one development of this embodiment, a size of unscaled optotypes in unscaled digital image data is scaled to the target size under consideration of the individual test dot pitch, by means of the rule of three, to provide the digital optotype image data. The unscaled digital image data thereby include images of unscaled optotypes. If these unscaled digital image data were to be displayed on the display surface, the displayed optotypes would not have the individual target size (unless they were to have the correct size purely at random). With knowledge of the individual test dot pitch, the unscaled digital image data are brought by means of the rule of three to the individual target size in which they should appear at the individual test distance. The digital optotype image data are thereby generated that are normally scaled and individually matched to the individual test distance. The rule of three offers a mathematically simple and easily calculated possibility to scale prepared, unscaled digital image data to the individual target size. Alternatively, similar mathematical methods may be used that enable a correct scaling.

According to one embodiment, a digital test image that is evaluated to detect the individual test distance is taken by means of an exposure device. The digital test image may be taken either from the test subject position, across the individual test distance in the direction of the display position, or from the display position in the direction of the test subject position. The digital test image is thus taken across the individual test distance. A camera—in particular a digital camera that automatically or semi-automatically creates digital images that may be evaluated by a computer—may be used as an exposure device. In the evaluation of the digital test image, the individual test distance is determined and provided as a determined variable for the further method. Alternatively, the individual test distance might also be determined by means of another distance detector and be input either automatically or manually.

In one development of this embodiment, the method has the steps:

arrange a calibration object such that the calibration object is spaced at the individual test distance from the exposure device, and take the test image such that the test image includes an exposure of the calibration object arranged at the individual test distance.

An arbitrary object given which the spacing of two prominent object points is known beforehand may serve as a calibration object. For example, a black square with known side length may serve as a calibration object, or a similar object given which at least two object points may be automatically detected (for example in a digital image evaluation). In the exposure of the test image, the calibration object is arranged at the individual distance from the exposure device. In particular, it may thereby be arranged so that the separated prominent object points of the calibration object are aligned orthogonal to the direction vector of the test distance from the test subject position to the display position. In the example of a two-dimensional black square, for example, this two-dimensional black square could be kept flat on the display surface, and the test image could be an image of the display surface on which the calibration object is arranged. At least two prominent object points of the calibration object are identified and marked—either automatically or manually—in an image evaluation. The individual test distance is calculated and thereby determined from the size of the spacing of the prominent object points of the calibration object in the digital test image.

In one development of this embodiment, a computer-controlled projection surface is used as a display surface, and the test image is taken from the test subject position so that the test image at least partially includes an exposure of the projection surface. "Computer-controlled" thereby means that digital data may be displayed on the projection surface. For example, a display arranged on a wall, a freestanding monitor, a screen (for a projector, for example), a room wall (for a video projector) etc. may be used as such a projection surface. Computer-generated image data may be displayed on the projection surface, in particular the provided digital optotype image data. The test image thereby at least partially includes an exposure of the projection surface.

In one development of this embodiment, a test image projected onto the projection surface is used to determine the individual test dot pitch. An exposure of the projected test image may thereby be taken, in particular a digital exposure with the exposure device. In particular the digital test image, which is evaluated to determine the individual test distance, may be used to determine the individual test dot pitch. In evaluation of a single test image, both the individual test distance and the individual test dot pitch may be determined and/or calculated in digital image data. In this case, the digital test image may include both the test image and the calibration object. For example, a single-color, complete illumination of the projection surface may serve as a particularly simple embodiment of the test image. The size of the entire projection surface in the acquired image data may thereby be measured, determined and/or provided, from which the individual test dot pitch may be determined. The test image may include at least two prominent image points that, for example, are detected quickly and with certainty (manually or automatically) in a digital image evaluation.

In an alternative embodiment, the display of a computer is used as a display surface, and the test image may be taken by a digital camera internal to the computer. In particular, tablet computers or laptops often have computer-internal digital cameras that may be used to detect the individual test distance. In particular, that computer-internal digital camera that is arranged at the height of and at the side of the computer display may be used. In this embodiment, this computer-internal digital camera is thus arranged at the display position and/or at a previously known, fixed position relative to the display position. An exposure of the test subject, who is arranged at the test subject position, may thus be made by the computer-internal digital camera.

In the embodiment described above, in which an external projection surface is used as a display surface, for example, the test image may also be taken by means of a computer-internal digital camera, whereby the test image is provided directly and very quickly to the computer for further processing.

In a development of the embodiment with the display as a display surface, refraction spectacles which the test subject wears when taking the test image may be used as a calibration object. Refraction spectacles which the test subject wears when conducting the vision test are typically necessary anyway to conduct the planned vision test. To detect the test distance, two prominent object points on the refraction spectacles may be used whose spacing relative to one another is fixed during the calibration process and thus is not variable. For this, for example, commercially available refraction spectacles may be used given which such prominent object points are easily detectable, and/or special markings may be arranged on any pair of refraction spectacles. Static points of the refraction spectacles whose spacing relative to one another is independent of a current adjustment of the refraction spectacles (such as an interpupillary distance etc.) may thereby be used as object points. The spacing of the markings relative to one another is known in advance and may be marked and/or determined either manually or automatically in the digital test image. The individual test distance can be determined from the spacing of the markings or object points of the refraction spectacles in the digital test image.

In a development of the embodiment, the digital optotype image data are scaled to the individual target size under consideration of the pixel size of the display as an individual test dot pitch. Since, in this embodiment, the display of the computer is used as a display surface, the individual test dot pitch does not necessarily need to be determined specifically; rather, it may be provided by the manufacturer of the computer, for example. The pixel pitch may also be verified as a control. Given use of the display of the computer, the individual test dot pitch must only be determined once, wherein the computer itself serves as a device for implementing the method that is set up at the individual test distance from the test subject.

According to one embodiment, an ambient brightness is detected, and the brightness of the displayed optotypes and/or the brightness of the immediate environment of the displayed optotypes on the display surface is adapted to the detected ambient brightness upon displaying the digital optotype image data. For example, the display brightness may be adapted so that interfering influences on the vision analysis—such as glare and/or adulteration due to dissolving of optotypes, as well as scatter effects at refractive media (refraction lenses, for example)—are reduced. The contrast and/or the brightness of the depicted optotypes and/or their environment may thereby be adapted to standardized reference values that, for example, are specified in the standards cited further above.

In one embodiment, the individual test distance is from one meter to ten meters. An individual test distance of four meters up to six meters is particularly preferably used. A different test distance may thereby be used and set for each measurement.

According to one embodiment, the method is implemented for different individual test distances, and digital optotype image data that include optotypes scaled to the individual target size are provided for each individual test distance. A determination of distance visual acuity that is matched to an individual, dynamically variable test distance may be conducted with one and the same device.

One aspect concerns a method for determining optical correction values of a test subject in which optotypes for a determination of distance visual acuity are provided according to the aspect described in the preceding, wherein the test subject attempts to recognize the provided optotypes by viewing from the test subject position, and the result of the viewing is [sic] input into a computer. This enables an automatic evaluation of the determination of visual acuity by means of the computer. A mobile computer may be used for this, for example. In particular, the computer with which the detection of the individual test distance etc. is implemented serves as a computer. The input takes place via an input interface of the computer, for example via a keyboard and/or via a touchscreen. The result may either be input into the computer by the test subject himself, be dictated by a tester, and/or be input by means of a remote control. The computer may subsequently display an evaluation of the test for determination of visual acuity, in particular regarding visual acuity, contrast capability, accommodation capability, color vision and/or binocular status of the test subject. The method may furthermore include additional vision tests, for example a determination of close visual acuity.

One aspect concerns a computer program product that has program parts which, when loaded into a computer, are designed to implement a computer-implemented method according to any of the aspects described in the preceding. For example, the computer program product may be a computer program, an app and/or a digital storage on which the computer program product is stored. The computer program product may thereby be designed and provided in particular to implement the following steps of the method according to any of the aspects described in the preceding:

detect an individual test distance between the test subject position and the display position, determine an individual target size for optotypes that are matched to the detected individual test distance according to a predetermined rule, provide digital optotype image data that include optotypes scaled to the individual target size, and display the digital optotype image data on the display surface.

Preceding method steps, for example the provision of the test subject position and the display surface at the display position, may be implemented by an operating personnel. The computer program product thus in particular serves to assist in the implementation of the method by an operating personnel.

The computer program product may thereby in particular be designed and provided to acquire a digital test image by means of an exposure device, which test image is evaluated automatically or semi-automatically, for example, to detect the individual test distance.

A calibration object may thereby be arranged by an operating personnel such that the calibration object is at the individual test distance from the exposure device.

The computer program product may be designed and provided to acquire the test image such that the test image includes an exposure of the calibration object arranged at the individual test distance.

One aspect concerns a device for implementation of the method described in the preceding. For example, such a device may have a mobile computer with a computer-internal digital camera, which mobile computer has a computer program product according to the preceding aspect.

The invention is described in the following using individual features of some exemplary embodiments, without a preferred order.

Via the subject matters of the independent Claims, a determination of visual acuity is provided for a variable test distance and for a plurality of different vision tests. A determination of visual acuity may be implemented both in a refraction room at a physician, optician etc., and given a house call, in hospitals and at events.

The possibility exists that the test subject himself may select and input at a control element the optotypes that he recognizes, whereupon the input may be automatically checked for accuracy. For example, a testing optician is thereby not himself dependent on good visual acuity since the automatic querying of the recognition of optotypes is facilitated for him.

If the invention is implemented by means of a computer, the computer may have an interface for a branch software. Determined refraction data may be transmitted automatically or manually to the branch software via the interface. For example, spectacles may thereby be ordered and/or their availability and/or price may be queried.

Cost-intensive, non-transportable vision test devices may be replaced with the proposed solution. An all-in-one alternative to the vision test devices that have been known until now is provided that, due to its mobile use capability and cost-effectively procurement, may also be used in developing countries, for example.

One embodiment concerns a device for implementing a determination of visual acuity with a mobile computer. The mobile computer has an input unit, a visual output unit and a digital camera. The device may be coupled with external display and/or a projection surface (activated by a projector) as a display surface. In this case, the contents displayed on the display surface are controlled and/or regulated via the input and/or output unit of the mobile computer. Alternatively or additionally, the mobile computer may be used alone, wherein the visual output unit (for example a display) serves as a display surface. A computer program product installed on the mobile computer may include a corresponding selection of the display surface, or be designed and provided for a predetermined one of the two alternatives.

An input unit of the computer may be used to control the display contents and/or for feedback about implemented testing tasks.

In one embodiment, a calibration object having at least partially known dimensions is used to determine the test distance. A digital test image of the calibration object is thereby made, which calibration object is thereby arranged in the display plane. The individual test dot pitch—for example the actual real spacing of two image points on a computer-controlled projection surface—may be determined from the at least partially known dimensions of the calibration object in the digital test image.

Given use of the refraction spectacles as a calibration object, which refraction spectacles are used for determination of visual acuity, the refraction spectacles can be individually adjusted to the test subject. For example, the refraction spectacles may be adjusted to the individual interpupillary distance of the test subject. Markings for adjustment of the interpupillary distance (for example an inner edge of the lens mounts, or specifically attached elements such as, for example, blue balls given the Oculus UB-4 refraction spectacles) may be used as well-defined, distinguished and/or prominent points of the refraction spectacles as a calibration object.

The distance of the calibration object from the exposure device, which corresponds to the individual test distance, may be determined by means of an established calibration that indicates a correlation between the actual object distance from the exposure device on the one hand and the pitch in pixels in the test image of the exposure device on the other hand.

A more high-contrast printout—for example a black geometric object (square, for example) that is surrounded by a white border—may be used as a calibration object. The printout may be attached to the display surface for the exposure of the test image described above.

For calibration, at least one calibration exposure of the calibration object may respectively be made at multiple defined distances from the exposure device. A correlation between the defined distances and the size of the calibration object in the images taken with the exposure device may be established from the pixel pitches of prominent object points in the respective calibration exposures. With the aid of this calibration (thus this correlation), the individual test distance may be determined from the digital test image that includes an exposure of the calibration object.

In the determination of visual acuity, optotypes are shown to the test subject. The test subject attempts to correctly recognize the optotypes. This solution to the vision test provided by means of the optotypes (for example the direction of the opening in Landolt rings), as recognized by the test subject, may be fed back via an input interface of the computer by either the test subject or a testing personnel. From this feedback, using a comparison (implemented by the computer) with the displayed vision tasks it may be determined whether the vision tasks have been solved correctly, thus for example if the optotypes have been correctly recognized by the test subject. A conclusion about the vision capability of the test subject—for example his visual acuity, his contrast vision etc.—may be made from a plurality of such feedback. For example, an automatic sequence of vision tasks may be used and/or provided for this.

Optotypes and test contents may thereby be displayed independent of distance and in variable size. Via a simple and fast calibration, the application to the spatial conditions is adapted in order to conduct a vision test, for example in a display conforming to standards.

A mobile computer may thereby serve as a control element. The mobile computer on its own may be used as a refraction device, possibly together with a remote control for inputting feedback of the test subject. The mobile computer may thereby be set up at an arbitrary test distance from the test subject, but preferably at an arbitrary test distance from 1 m to 10 m.

The mobile computer may be used as a mobile refraction unit and/or as a software platform for a projection device that may be arranged as a local unit at the test site. Both a local use and an additional mobile use of the mobile computer for a stationary and mobile refraction are thereby enabled with the same core elements.

A correction of the imaging errors of the camera optic that is used may be determined for the exposure device that is used, which imaging errors may be corrected in the exposure of the images (test image, calibration exposure etc.).

The invention claimed is:

1. A method for providing optotypes for a determination of distance visual acuity, comprising:
   providing a test subject position for a test subject;
   providing a display surface at a display position;
   detecting an individual test distance between the test subject position and the display position;
   determining an individual target size for optotypes that are matched to the detected individual test distance according to a predetermined rule;
   providing digital optotype image data that include optotypes scaled to the individual target size;
   displaying the digital optotype image data on the display surface;
   arranging a calibration object such that the calibration object is at the individual test distance from an exposure device;
   taking a digital test image taken by means of the exposure device such that the test image includes an exposure of the calibration object arranged at the individual test distance; and
   evaluating the digital test image to detect the individual test distance.

2. The method according to claim 1, wherein the determination of the individual target size for optotypes, the providing of the digital optotype image data, and the displaying of the digital optotype image data are implemented automatically by means of a mobile computer.

3. The method according to claim 1, wherein an individual test dot pitch in digital image data is determined at the display surface, and
   wherein the digital optotype image data are scaled to the individual target size under consideration for the individual test dot pitch.

4. The method according to claim 3, wherein a size of unsealed optotypes in unsealed digital image data is scaled under consideration of the individual test dot pitch, by means of the rule of three, to provide the digital optotype image data in the individual target size.

5. The method according to claim 1, wherein a computer-controlled projection surface is used as the display surface, and
   wherein the test image is taken from the test subject position so that the test image includes an exposure of the computer-controlled projection surface.

6. The method according to claim 1, wherein a test image projected onto the computer-controlled projection surface is evaluated to determine an individual test dot pitch.

7. The method according to claim 1, wherein the display of a computer is used as the display surface, and
   wherein the test image is taken by a computer-internal digital camera of the computer.

8. The method according to claim 1, wherein refraction spectacles that the test subject wears upon viewing the test image are used as a calibration object.

9. The method according to claim 7, wherein the digital optotype image data are scaled to the individual target size under consideration of the pixel size of the display as an individual test dot pitch.

10. The method according to claim 1, wherein an ambient brightness is detected; and
    in displaying the digital optotype image data, a brightness of the displayed optotypes or a brightness of the immediate environment of the displayed optotypes on the display surface is adapted to the detected ambient brightness.

11. The method according to claim 1, wherein the individual test distance is between 1 meter and 10 meters.

12. The method according to claim 1, wherein the method is repeated for different individual test distances, and
    wherein digital optotype image data that include optotypes scaled to the individual target size are provided for each of the different individual test distances.

13. The method according to claim 1, wherein the test subject attempts to recognize the provided optotypes via viewing from the test subject position, and further comprising:
   inputting the result of the viewing are into a computer.

14. A computer program product having program parts which, when loaded into a computer, are designed to implement a computer-implemented method according to claim 1.

15. A mobile computer having a computer-internal digital camera, which mobile computer has a computer program product according to claim 14.

16. The method of claim 1, wherein the individual test distance is determined from a size of a spacing of two prominent object points of the calibration object in the digital test image.

* * * * *